United States Patent
Lodin et al.

(10) Patent No.: US 8,084,058 B2
(45) Date of Patent: Dec. 27, 2011

(54) PHARMACEUTICAL FORMULATION CONTAINING A BIGUANIDE AND A THIAZOLIDINEDIONE DERIVATIVE

(75) Inventors: Unchalee Lodin, North Miami Beach, FL (US); Jack Cardinal, Tamarac, FL (US); Avinash Nangia, Lincoln, RI (US)

(73) Assignees: Watson Pharmaceuticals, Inc., Corona, CA (US); Takeda Pharmaceutical, Co. Ltd., Osaka (JP)

( * ) Notice: Subject to any disclaimer, the term of this patent is extended or adjusted under 35 U.S.C. 154(b) by 1072 days.

(21) Appl. No.: 11/094,493

(22) Filed: Mar. 30, 2005

(65) Prior Publication Data

US 2005/0249809 A1 Nov. 10, 2005

Related U.S. Application Data

(63) Continuation-in-part of application No. 10/777,542, filed on Feb. 12, 2004, now Pat. No. 7,959,946, which is a continuation-in-part of application No. 10/664,803, filed on Sep. 19, 2003, now Pat. No. 7,785,627.

(60) Provisional application No. 60/412,180, filed on Sep. 20, 2002, provisional application No. 60/412,181, filed on Sep. 20, 2002.

(51) Int. Cl.
*A61K 9/24* (2006.01)
*A61K 31/426* (2006.01)
*A61K 31/155* (2006.01)

(52) U.S. Cl. .......... 424/472; 514/369; 514/635

(58) Field of Classification Search .......... 424/472; 514/369, 635

See application file for complete search history.

(56) References Cited

U.S. PATENT DOCUMENTS

| | | |
|---|---|---|
| 3,174,901 A | 3/1965 | Sterne |
| 3,960,949 A | 6/1976 | Ahrens et al. |
| 4,166,800 A | 9/1979 | Fong |
| 4,389,330 A | 6/1983 | Tice et al. |
| 4,687,777 A | 8/1987 | Meguro et al. |
| 4,839,177 A | 6/1989 | Colombo et al. |
| 4,891,223 A | 1/1990 | Ambegaonkar et al. |
| 4,968,507 A | 11/1990 | Zentner et al. |
| 5,294,770 A | 3/1994 | Riddle et al. |
| 5,356,913 A | 10/1994 | Colca |
| 5,376,771 A | 12/1994 | Roy |
| 5,478,852 A | 12/1995 | Olefsky et al. |
| 5,602,133 A | 2/1997 | Antonucci et al. |
| 5,658,474 A | 8/1997 | Geerke |
| 5,681,584 A | 10/1997 | Savastano et al. |
| 5,698,220 A | 12/1997 | Cardinal et al. |
| 5,719,188 A | 2/1998 | Colca |
| 5,840,335 A | 11/1998 | Wenzel et al. |
| 5,859,037 A | 1/1999 | Whitcomb |
| 5,916,584 A | 6/1999 | O'Donoghue et al. |
| 5,948,440 A | 9/1999 | Arora et al. |
| 5,952,356 A | 9/1999 | Ikeda et al. |
| 5,955,106 A | 9/1999 | Moeckel et al. |
| 5,965,584 A | 10/1999 | Ikeda et al. |
| 6,011,049 A | 1/2000 | Whitcomb |
| 6,031,004 A | 2/2000 | Timmins et al. |
| 6,099,859 A | 8/2000 | Cheng et al. |
| 6,099,862 A | 8/2000 | Chen et al. |
| 6,153,632 A | 11/2000 | Rieveley |
| 6,166,042 A | 12/2000 | Ikeda et al. |
| 6,166,043 A | 12/2000 | Ikeda et al. |
| 6,172,090 B1 | 1/2001 | Ikeda et al. |
| 6,191,162 B1 | 2/2001 | Byrd et al. |
| 6,248,363 B1 | 6/2001 | Patel et al. |
| 6,291,495 B1 | 9/2001 | Rieveley |
| 6,296,874 B1 | 10/2001 | Cutie et al. |
| 6,329,403 B1 | 12/2001 | Odaka et al. |
| 6,383,471 B1 | 5/2002 | Chen et al. |
| 6,403,121 B1 | 6/2002 | Adjei et al. |
| 6,451,342 B2 | 9/2002 | Adjei et al. |
| 6,475,521 B1 | 11/2002 | Timmins et al. |
| 6,495,162 B2 | 12/2002 | Cheng et al. |
| 6,524,621 B2 | 2/2003 | Adjei et al. |
| 6,599,284 B2 | 7/2003 | Faour |
| 6,660,300 B1 | 12/2003 | Timmins et al. |
| 6,780,432 B1 | 8/2004 | Cutie et al. |
| 6,790,459 B1 | 9/2004 | Cheng et al. |
| 6,838,093 B2 | 1/2005 | Flanner et al. |
| 6,866,866 B1 | 3/2005 | Chen et al. |
| 7,374,779 B2 * | 5/2008 | Chen et al. .......... 424/451 |
| 2001/0046515 A1 | 11/2001 | Adjei et al. |
| 2002/0064556 A1 | 5/2002 | Cheng et al. |

(Continued)

FOREIGN PATENT DOCUMENTS

CN 1582928 A 2/2005

(Continued)

OTHER PUBLICATIONS

Koski, "Review of Oral Antihyperglycemic Agents," Diabetes Educator, 32(6):869-874.*
Finnish Monograph of the Diformin®, Retard tablet, with English translation.
O.J. Lucis, MD, Ph.D., MSC, Canada Medical Association J. Pharmacologic Update "The status of metformin in Canada" vol. 128, Jan. 1, 1983, pp. 24-26.
ADA Professional Section Member Supplement 0474 and 0503-506 (Poster) p. A110; A117.
ACTOS® product label, Physician's Desk Reference, 55th Edition, pp. 3171-3175.

(Continued)

*Primary Examiner* — Shaojia Anna Jiang
*Assistant Examiner* — Jonathan S Lau
(74) *Attorney, Agent, or Firm* — Florek & Endres PLLC

(57) ABSTRACT

A pharmaceutical dosage form comprising a controlled release component comprising an antihyperglycemic drug in combination with a second component comprising a thiazolidinedione derivative and a disintegrating agent is herein disclosed and described. The dosage formulation exhibits a significant increase in bioavailability of the thiazolidinedione derivative component compared to conventional immediate release dosage forms containing only a thiazolidinedione derivative.

4 Claims, 4 Drawing Sheets

U.S. PATENT DOCUMENTS

| | | | |
|---|---|---|---|
| 2002/0071866 A1 | 6/2002 | Geerke | |
| 2003/0077297 A1 | 4/2003 | Chen et al. | |
| 2003/0113371 A1 | 6/2003 | Dhawan et al. | |
| 2003/0118647 A1 | 6/2003 | Seth | |
| 2003/0118649 A1 | 6/2003 | Gao et al. | |
| 2003/0224046 A1 | 12/2003 | Rao et al. | |
| 2004/0081697 A1 | 4/2004 | Lewis et al. | |
| 2004/0092531 A1 | 5/2004 | Chizh et al. | |
| 2005/0074490 A1 | 4/2005 | Lin et al. | |
| 2006/0057202 A1* | 3/2006 | Antarkar et al. | 424/472 |
| 2006/0141023 A1 | 6/2006 | Trehan et al. | |
| 2006/0204578 A1* | 9/2006 | Vergez et al. | 424/473 |
| 2006/0286168 A1 | 12/2006 | Koike et al. | |

FOREIGN PATENT DOCUMENTS

| | | |
|---|---|---|
| EP | 0 169 105 | 1/1986 |
| EP | 0 283 369 | 9/1988 |
| EP | 0 381 181 | 8/1995 |
| EP | 0 749 751 | 12/1996 |
| EP | 0 781 129 | 7/1997 |
| EP | 0 753 298 | 11/2001 |
| EP | 1 588 708 A1 | 10/2005 |
| WO | WO 96/09823 | 4/1996 |
| WO | WO 98/11879 | 3/1998 |
| WO | WO 98/55107 | 12/1998 |
| WO | WO 99/47125 | 9/1999 |
| WO | WO 99/47128 | 9/1999 |
| WO | WO 99/55320 | 11/1999 |
| WO | WO 00/28989 | 5/2000 |
| WO | WO 00/72827 | 12/2000 |
| WO | WO 01/35940 | 5/2001 |
| WO | WO 01/35941 | 5/2001 |
| WO | WO01/47498 | 7/2001 |
| WO | WO01/74336 | 10/2001 |
| WO | WO 01/82875 | 11/2001 |
| WO | WO0211702 | 2/2002 |
| WO | WO 02/28181 | 4/2002 |
| WO | WO 03/004009 | 1/2003 |
| WO | WO 03/035029 | 5/2003 |
| WO | WO03/004355 | 6/2003 |
| WO | WO 03/047529 | 6/2003 |
| WO | WO 2004/006921 | 1/2004 |
| WO | WO 2004/067001 | 8/2004 |
| WO | WO 2005/063226 | 7/2005 |
| WO | WO 2005/110405 | 11/2005 |

OTHER PUBLICATIONS

An opposition filed in Costa Rica against a foreign equivalent of the present application.

A translation of the opposition filed in Costa Rica against a foreign equivalent of the present application.

A response to the opposition filed in Costa Rica against a foreign equivalent of the present application.

A translation of the response to the opposition filed in Costa Rica against a foreign equivalent of the present application.

An opposition filed in Chile against a foreign equivalent of the present application.

A translation of the opposition filed in Chile against a foreign equivalent of the present application.

A response to the opposition filed in Chile against a foreign equivalent of the present application.

A translation of the response to the opposition filed in Chile against a foreign equivalent of the present application.

An English translation of an opposition filed in Columbia against a related foreign application.

A response to the opposition filed in Columbia against a related foreign application (in Spanish).

An English translation of a response to the opposition filed in Columbia against a related foreign application.

A search report from the Georgian Patent Office (and English translation).

An Office Action from the Ukrainian Patent Office (and English translation).

Efficacy of Metabolic Effects of Metformin and Troglitazone in type II diabetes mellitus; Inzucchi Se et al. N. Engl. J Med. Mar. 26, 1998; 338(13): 867-72.

Effect of Metformin and Rosiglitazone combination therapy in patients with type II diabetes mellitus, Fonseca V, et al.; Apr. 5, 2000; 283(13): 1695-702.

Zimmer Barbara, Supplementary European Search Report, EP 03 75 4689, May 6, 2010, European Patent Office 80298 Munich, Germany.

Koski, Renee Rae, Practical Review of Oral Antihyperglycemic Agents for Type 2 Diabetes Mellitus, The Diabetes Educator 32 (6) 869-876 (Nov./Dec. 2006).

Jagoe, Donna, International Search Report, PCT/US03/29292, Apr. 26, 2004, ISA/US, Commissioner for Patents, P.O. Box 1450, Alexandria Virginia 22313-1450.

Jagoe, Donna, International Preliminary Examination Report, PCT/US03/29292, Jan. 4, 2005, IPEA/US, Commissioner for Patents, P.O. Box 1450, Alexandria Virginia 22313-1450.

Joynes, Robert M., International Search Report, PCT/US04/04112, Aug. 12, 2004, ISA/US, Commissioner for Patents, P.O. Box 1450, Alexandria Virginia 22313-1450.

Nickitas-Etienne, Athina, International Preliminary Report on Patentability, PCT/US2004/004112, Feb. 28, 2007, The International Bureau of WIPO, 34, chemin des Colombettes, 1211 Geneva 20, Switzerland.

Woodward, Michael, International Search Report and Written Opinion of the International Searching Authority, PCT/US06/09082, Jul. 20, 2006, ISA/US, Commissioner for Patents, P.O. Box 1450, Alexandria Virginia 22313-1450.

Menon, K.V, et al., Severe Cholestatic Hepatitis from Troglitazone in a Patient with Nonalcoholic Steatohepatitis and Diabetes Mellitus, The American J. of Gastroenterology, 96 (5) 1631-34 (2001).

Egger M., et al., Risk of Adverse Effects of Intensified Treatment in Insulin-Dependent Diabetes Mellitus: A Meta-Analysis; Diabetic Med. Nov. 1997; 14 (11): 919-28.

Dailey GE., Glyburide/Metformin Tablets: A New Therapeutic Option for the Management of Type 2 Diabetes. Expert Opinion Pharmacotherapy (2003) 4(8): 1417-30. Review. (Abstract Only).

Bailey CJ, et al. Avandamet: Combined Metformin-Rosiglitazone Treatment for Insulin Resistance in Type 2 Diabetes, Int J Clin Pract (Sep. 2004) 58(9): 867-76.

Campbell, RK et al., Metformin: A New Oral Biguanide, Clin Ther (May-Jun. 1996); 18(3): 360-71.

Davidson, MB, et al., An Overview of Metformin in the Treatment of Type 2 Diabetes Mellitus, Am J Med. (Jan. 1997); 102(1):99-110.

Dunn, CJ, et al., Metformin. A Review of its Pharmacological Properties and Therapeutic Use in Non-Insulin-Dependent Diabetes Mellitus, Drugs (May 1995); 49(5):721-49.

P. Karttunen et al., International Journal of Clinical Pharmacology, Therapy and Toxicology, "The pharmacokinetics of metformin: a comparison of the properties of a rapid release and a sustained-release preparation" vol. 21, No. 1—1983, pp. 31-36.

P.J. Pentikainen, International Journal of Clinical Pharmacology, Therapy and Toxicology, "Bioavailability of metformin. Comparison of solution, rapidly dissolving tablet, and three sustained release products", vol. 24, No. 4—1986, pp. 213-220.

Finnish Monograph of the Diformin®, Retard tablet, with English translation, pub date 2004.

O.J. Lucis, MD, Ph.D., MSC Canada Medical Association J. Pharmacologic Update "The status of metformin in Canada" vol. 128, Jan. 1, 1983, pp. 24-26.

G. Belcher and D.R. Matthews, Experiment and Clinical Endrocrinology & Diabetes, "Safety and tolerability of pioglitazone" Suppl. 2 (2000) pp. 267-273.

Daniel Einhorn, MD et al., Clinical Therapeutics "Pioglitazone Hydrochloride in Combination with Metformin in the Treatment of Type 2 Diabetes Mellitus: a Randomized, Placebo-Controlled Study", vol. 22, No. 12, 2000 pp. 1395-1413.

National Institute for Clinical Excellence Technology Appraisal Guidance—No. 21, "Guidance on the Use of Pioglitazone for Type 2 Diabetes Mellitus" Mar. 2001, pp. 1-13.

The Pharmaceutical Journal, vol. 265, No. 7122, p. 710 Nov. 11, 2000 Clinical (abstract only).

Product Labeling for Glucophage® XR (Jul. 2002).

ADA Professional Section Member Supplement 0474 and 0503-506 (Poster) p. A110; A117, pub date 2001.

Website www.findarticles.com, Clinician Reviews, "Insulin-Sensitizing Diabetes Agent" Sep. 1999.

ACTOS® product label, Physician's Desk Reference, 55th Edition, pp. 3171-3175, pub. date 2001.

Rote Liste No. 11081 the Medicament MEDIABET of Medice; GLUCOBAY of Bayer; and GLUCOTARD of Boehringer Mannheim, Chem.-Pharm. Fabrik Pütter GmbH & Co. KG, Kuhloweg 37-39 Iserlohn/Germany, Editio Cantor Verlag für Medizin und Naturwissenschaften GmbH, 1993.

Abdallah et al., "Preparation and Evaluation of Metformin Hydrochloride Controlled-Release Tablets" STP Pharma 4(1) pp. 15-20, 1988.

An opposition filed in Costa Rica against a foreign equivalent of the present application., Feb. 20, 2008.

A translation of the opposition filed in Costa Rica against a foreign equivalent of the present application, Feb. 20, 2008.

A response to the opposition filed in Costa Rica against a foreign equivalent of the present application, Apr. 24, 2008.

A translation of the response to the opposition filed in Costa Rica against a foreign equivalent of the present application, Apr. 24, 2008.

An opposition filed in Chile against a foreign equivalent of the present application, Nov. 22, 2007.

A translation of the opposition filed in Chile against a foreign equivalent of the present application, Aug. 17, 2007.

A response to the opposition filed in Chile against a foreign equivalent of the present application, Jan. 30, 2008.

A translation of the response to the opposition filed in Chile against a foreign equivalent of the present application, Jan. 30, 2008.

* cited by examiner

PHARMACEUTICAL FORMULATION CONTAINING A BIGUANIDE AND A THIAZOLIDINEDIONE DERIVATIVE

This is a continuation-in-part application of U.S. patent application Ser. No. 10/777,542 filed on Feb. 12, 2004 now U.S. Pat. No. 7,959,946 which is a continuation-in-part application of U.S. patent application Ser. No. 10/664,803 filed on Sep. 19, 2003 now U.S. Pat. No. 7,785,627 and which claims the benefit of U.S. provisional patent application Ser. Nos. 60/412,180 and 60/412,181 filed on Sep. 20, 2002.

BACKGROUND OF THE INVENTION

The present invention relates to a pharmaceutical dosage form comprising an antihyperglycemic drug, in combination with a thiazolidinedione derivative. More specifically, the present invention relates to an oral dosage form comprising a biguanide e.g. metformin or buformin or a pharmaceutically acceptable salt thereof e.g., metformin hydrochloride or the metformin salts described in U.S. Pat. Nos. 3,957,853 and 4,080,472 which are incorporated herein by reference in combination with a thiazolidinedione derivative as described in U.S. Pat. No. 4,687,777 also incorporated herein by reference.

Many techniques have been used to provide controlled and extended-release pharmaceutical dosage forms in order to maintain therapeutic serum levels of medicaments and to minimize the effects of missed doses of drugs caused by a lack of patient compliance.

For example, extended release tablets have been described which have an osmotically active drug core surrounded by a semipermeable membrane. These tablets function by allowing the aqueous component of a fluid such as gastric or intestinal fluid to permeate the coating membrane and dissolve the active ingredient so the resultant drug solution can be released through a passageway in the coating membrane. Alternatively, if the active ingredient is insoluble in the permeating fluid, it can be pushed through the passageway by an expanding agent such as a hydrogel. Some representative examples of these osmotic tablet systems can be found in U.S. Pat. Nos. 3,845,770; 3,916,899; 4,034,758; 4,077,407 and 4,783,337. U.S. Pat. No. 3,952,741 teaches an osmotic device wherein the active agent is released from a core surrounded by a semipermeable membrane only after sufficient pressure has developed within the membrane to burst or rupture the membrane at a weak portion of the membrane.

The basic osmotic device described in the above cited patents have been refined over time in an effort to provide greater control of the release of the active ingredient. For example, U.S. Pat. Nos. 4,777,049 and 4,851,229 describe osmotic dosage forms comprising a semipermeable wall surrounding a core. The core contains an active ingredient and a modulating agent wherein the modulating agent causes the active ingredient to be released through a passageway in the semipermeable membrane in a pulsed manner. Further refinements have included modifications to the semipermeable membrane surrounding the active core such as varying the proportions of the components that form the membrane, e.g. U.S. Pat. Nos. 5,178,867, 4,587,117 and 4,522,625 or increasing the number of coatings surrounding the active core, e.g. U.S. Pat. Nos. 5,650,170 and 4,892,739.

Certain controlled or sustained release formulations that employ antihyperglycemic drugs such as metformin hydrochloride have been limited to the use of an expanding or gelling agent to control the release of the drug from the dosage form. This limited research is exemplified by the teachings of WO 96/08243 and by the GLUCOPHAGE™ XR product insert which is a controlled release metformin HCl product commercially available from Bristol-Myers Squibb Co.

Thiazolidinedione derivatives have been described in U.S. Pat. No. 4,687,777. The therapeutic value of these compounds in combination therapy has further been described in U.S. Pat. Nos. 5,859,037; 5,952,356; 5,965,584; 6,150,384 and 6,172,090. However, none of these patents describe a dosage form having the advantages of the subject invention.

Pharmaceutical dosage forms containing combinations of antihyperglycemic drugs and thiazolidinedione derivatives have been proposed in the art. For example, EPO 0 749 751 (which is incorporated herein by reference) teaches pharmaceutical compositions comprising an insulin sensitivity enhancer, which could be a thiazolidinedione compound, in combination with other antidiabetics. More specifically, EPO 0 749 751 teaches that the preferred insulin sensitivity enhancer is pioglitazone, which can be combined with other antidiabetics such as metformin, phenformin or buformin, and further that these drugs can be associated (mixed and/or coated) with conventional excipients to provide taste masking or sustained release behavior. Another example of a combination of antihyperglycemic drugs and thiazolidinedione derivatives is U.S. Pat. No. 6,011,049, (which is incorporated herein by reference). This patent teaches a single pharmaceutical composition that contains pioglitazone or troglitazone and metformin in slow release forms such as osmotic pumps or skin patches. Other combinations of antihyperglycemic drugs and thiazolidinedione derivatives can be found in U.S. Pat. Nos. 6,524,621; 6,475,521; 6,451,342 and 6,153,632 and PCT patent applications WO 01/35940 and WO 01/35941, which are incorporated herein by reference.

Also known in the art are WO 99/47125 and U.S. Pat. No. 6,099,862 that disclose a metformin osmotic tablet coated with an immediate release coating containing an antihyperglycemic or a hypoglycemic drug.

Although the prior art teaches pharmaceutical dosage formulations that contain both an antihyperglycemic compound and thiazolidinedione derivatives, the present invention provides numerous benefits over the prior art teachings as will be described below.

The present invention further provides for a dosage formulation that comprises a first and second active drug wherein the dosage formulation exhibits a significantly increased or higher bioavailability of the second active drug, which preferably is a thiazolidinedione derivative, when compared to a conventional immediate release dosage form that contains only the second active drug.

It is an object of the present invention to provide a dosage form comprising a first active drug, which is formulated to provide a controlled or sustained release delivery. Preferably, the first active drug is an antihyperglycemic compound. The present invention further provides for a second active drug that preferably is a thiazolidinedione derivative. The novel dosage form described herein provides for delivery of first and second active drugs such that the bioavailability of either drug is not decreased by the presence of food.

It is a further object of the present invention to provide a dosage form, as described above, comprising delivery of a first active drug as a controlled or sustained release formulation for an antihyperglycemic compound, wherein said controlled or sustained release mechanism is not regulated by an expanding polymer, in combination with delivery of a second active drug by immediate release comprising a thiazolidinedione derivative.

It is also a further object of the present invention to provide a dosage form as described above, comprising delivery of a first active drug as a controlled or sustained release formulation for an antihyperglycemic compound in combination with delivery of a second active drug by immediate release comprising a thiazolidinedione derivative that can provide continuous and non-pulsating therapeutic levels of said antihyperglycemic drug to an animal or human in need of such treatment over a eight hour to twenty-four hour period.

It is an additional object of the present invention to provide a dosage form comprising delivery of a first active drug as a controlled or sustained release formulation for an antihyperglycemic compound in combination with delivery of a second active drug by immediate release comprising a thiazolidinedione derivative that obtains peak plasma levels of the antihyperglycemic compound approximately 8-12 hours after administration and peak plasma levels of thiazolidinedione derivative approximately 1-6 hours after dosing.

It is also an object of the present invention to provide a dosage form comprising a first active drug as a controlled or sustained release pharmaceutical core tablet having only a homogeneous osmotic core wherein the osmotic core component may be made using ordinary tablet compression techniques.

It is a further object of the present invention to provide a dosage form comprising an antihyperglycemic drug as a controlled or sustained release component and a thiazolidinedione derivative as an immediate release component, wherein not less than 85% of the total amount of the thiazolidinedione derivative is released from the dosage form within 45 minutes or less.

SUMMARY OF THE INVENTION

The present invention relates to a pharmaceutical dosage form comprising a first active drug, preferably an antihyperglycemic drug, in combination with a second active drug, preferably a thiazolidinedione derivative. More specifically, the present invention relates to an oral dosage form comprising a first active drug comprising a biguanide such as metformin or buformin or a pharmaceutically acceptable salt thereof e.g., metformin hydrochloride or the metformin salts, in combination with a second active drug comprising a thiazolidinedione derivative.

The foregoing objectives are met by a dosage form comprising a first and second active drug, wherein the first active drug is formulated as a controlled release core, preferably an osmotic tablet, with or without a gelling or expanding polymer. The second active ingredient is combined with the controlled release core in a manner that provides for immediate release of the second active ingredient. For example, the second active ingredient can be incorporated into a membrane that is applied to the core or the second active ingredient may be applied to a coated or uncoated controlled release core.

In one embodiment the second active drug, which may be the thiazolidinedione derivative, is provided as an immediate release formulation in the dosage form whereas the antihyperglycemic component is provided as a controlled release formulation in the dosage form. This immediate release portion of the formulation should contain the thiazolidinedione derivative and a pharmaceutically acceptable disintegrating agent and should provide peak plasma levels ($T_{max}$) 1-6 hours, preferably 1-4 hours after administration of the thiazolidinedione derivative, while the controlled release portion of the formulation may provide peak plasma levels ($T_{max}$) of 4-12 hours, preferably 6-10 hours after administration of the antihyperglycemic component with a meal.

Preferably, the dosage form according to the subject invention may be administered once a day, preferably with or after a meal, and most preferably with or after the evening meal. The subject dosage form can provide therapeutic levels of the drug throughout the day with peak plasma levels ($T_{max}$) of the antihyperglycemic drug being obtained between 4-12 hours after administration.

As used in this specification, the phrases "significantly increased bioavailability", "significantly higher bioavailability" "increased bioavailability" and "higher bioavailability" are used interchangeably and refer to a maximum serum concentration level ($C_{max}$) and/or the area under the serum concentration curve (AUC) of a pharmaceutically active component of the dosage formulation. The increase or higher bioavailability is determined by conducting an in vivo test that employs standard pharmacokinetic methodology that is well known in the art and compares the subject dual pharmaceutically active dosage formulation to a conventional immediate release dosage form that contains only one of the dual pharmaceutically actives. The number of subjects in the in vivo study should be at least three.

The phrases "significantly increased bioavailability", "significantly higher bioavailability" "increased bioavailability" and "higher bioavailability" generally refer to a $C_{max}$ for the subject dual pharmaceutically active dosage formulation that is at least 120% greater, preferably 130% greater and most preferably 135% than the $C_{max}$ for the conventional immediate release dosage form that contains only one of the pharmaceutically actives components contained the dual pharmaceutically active dosage formulation. The terms also refer to an AUC for the subject dual pharmaceutically active dosage formulation that is at least 110% greater, preferably 115% greater and most preferably 120% than the AUC for the conventional immediate release dosage form that contains only one of the pharmaceutically actives components contained the dual pharmaceutically active dosage formulation.

As used herein the phrase "conventional immediate release dosage form" refers to a dosage form that releases at least 90% of its active ingredient within 30 minutes when tested according to the United States Pharmacopeia (USP) 26, with Apparatus 1 at 100 rpm, 37° C. and 900 ml of 0.3 M KCl—HCl Buffer, pH 2.0.

DETAILED DESCRIPTION OF THE INVENTION

Figure 1:
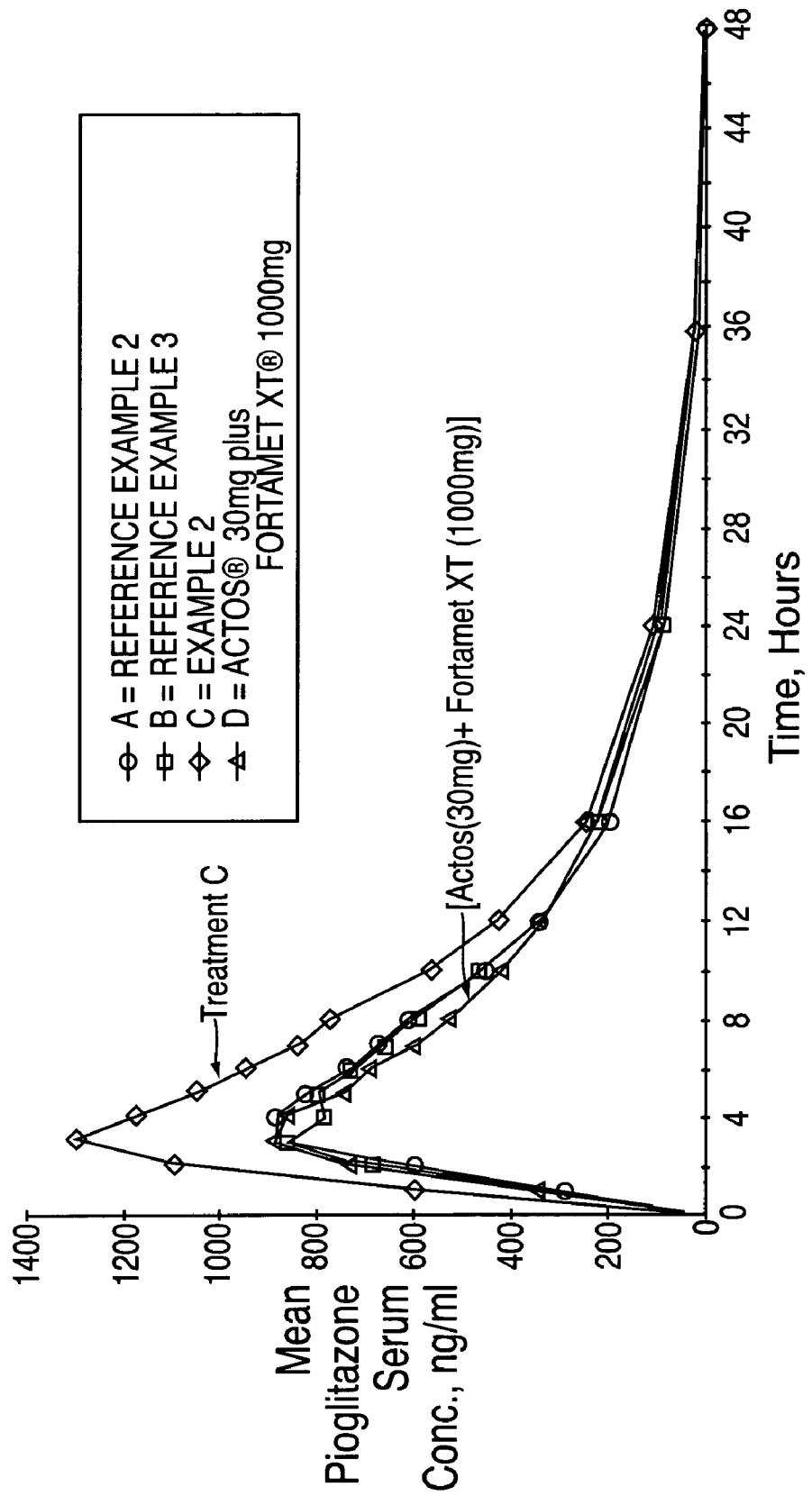
FIG. 1 is graph depicting the mean pioglitazone serum concentration over time for the dosage formulation prepared in Example 2 compared to three reference formulations.

The subject invention concerns a pharmaceutical formulation or dosage form comprising a first active drug comprising an antihyperglycemic drug in combination with a second active drug comprising a thiazolidinedione derivative. Preferably, the antihyperglycemic drug is a biguanide e.g. metformin or buformin or a pharmaceutically acceptable salt thereof. The antihyperglycemic drug is delivered in a controlled release manner from a tablet core, preferably an osmotic tablet core with or without a gelling or swelling polymer. The tablet core should include the antihyperglycemic drug and at least one pharmaceutically acceptable excipient. In one embodiment of the present invention the tablet core includes the antihyperglycemic drug, a binding agent and an absorption enhancer, and the tablet core is preferably coated with a polymeric coating to form a membrane around the tablet and drilled to create at least one passageway on one or both sides of the membrane. The second active drug comprises a thiazolidinedione derivative, and is preferably applied to the membrane of the tablet core and provides for the immediate release of said thiazolidinedione derivative.

The term, antihyperglycemic drugs as used in this specification, refers to drugs that are useful in controlling or managing noninsulin-dependent diabetes mellitus (NIDDM). Antihyperglycemic drugs include the biguanides such as metformin, phenformin or buformin or the like, and pharmaceutically acceptable salts, isomers or derivatives thereof.

The term thiazolidinedione derivative as used in this specification refers to drugs that are useful for controlling or managing NIDDM. These include, but are not limited to, troglitazone, rosiglitazone, pioglitazone, ciglitazone or the like, and pharmaceutically acceptable salts, isomers or derivatives thereof. See, e.g., U.S. Pat. No. 4,687,777.

The term binding agent refers to any conventionally known pharmaceutically acceptable binder such as polyvinyl pyrrolidone, hydroxypropyl cellulose, hydroxyethyl cellulose, hydroxypropyl methylcellulose, ethylcellulose, polymethacrylate, polyvinylalcohol and the like. Mixtures of the aforementioned binding agents may also be used. The preferred binding agents are water soluble materials such as polyvinyl pyrrolidone having a weight average molecular weight of 25,000 to 3,000,000. The binding agent may comprise approximately about 0 to about 40% of the total weight of the core and preferably about 3% to about 15% of the total weight of the core. In one embodiment, the use of a binding agent in the core is optional.

In a preferred embodiment, the core may optionally comprise an absorption enhancer. The absorption enhancer can be any type of absorption enhancer commonly known in the art such as a fatty acid, a surfactant (anionic, cationic, amphoteric), a chelating agent, a bile salt or mixtures thereof. Examples of some preferred absorption enhancers are lecithin, fatty acids such as capric acid, oleic acid and their monoglycerides, surfactants such as sodium lauryl sulfate, sodium taurocholate, sodium taurodeoxycholate and polysorbate 80, chelating agents such as citric acid, phytic acid, ethylenediamine tetraacetic acid (EDTA) and ethylene glycol-bis($\beta$-aminoethyl ether)-N,N,N,N-tetraacetic acid (EGTA). The core may comprise approximately 0 to about 20% of the absorption enhancer based on the total weight of the core and most preferably about 2% to about 10% of the total weight of the core.

In one embodiment of the present invention, which does not employ a gelling or swelling polymer, the core of the present invention is preferably formed by granulating an antihyperglycemic drug with a binding agent and compressing the granules with the addition of a lubricant and absorption enhancer into a tablet. The core may also be formed by dry granulating the core ingredients by passing them through a roller compactor and compressing the granules with the addition of a lubricant into tablets. Direct compression may also be employed for tableting. Other commonly known granulation procedures are known in the art. Additionally, other excipients such as lubricants, pigments or dyes may also be employed in the formulation of the subject invention.

The term gelling or swelling polymer refers to polymers that gel, swell or expand in the presence of water or biological fluids. Representative examples of gelling or swelling polymers are high molecular weight hydroxpropyl methylcellulose (such as METHOCEL® K100M, which is commercially available from Dow Chemical) and high molecular weight polyethylene oxides (such as POLYOX WSR 301, WSR 303 or WSR COAGULANT). Other gelling or swelling polymers are described in U.S. Pat. No. 4,522,625 (which is incorporated herein by reference).

The core formed as described herein, can be coated with a membrane or sustained release coating. Materials that are useful in forming the membrane or sustained release coating are ethylcellulose, cellulose esters, cellulose diesters, cellulose triesters, cellulose ethers, cellulose ester-ether, cellulose acylate, cellulose diacylate, cellulose triacylate, cellulose acetate, cellulose diacetate, cellulose triacetate, cellulose acetate propionate and cellulose acetate butyrate. Other suitable polymers are described in U.S. Pat. Nos. 3,845,770; 3,916,899; 4,008,719; 4,036,228 and 4,612,008 (which are incorporated herein by reference). The most preferred membrane or sustained release coating material is cellulose acetate comprising an acetyl content of 39.3 to 40.3%, and is commercially available from Eastman Fine Chemicals.

In an alternative embodiment, the membrane or sustained release coating can include one of the above-described polymers and a flux-enhancing agent. The flux enhancing agent can increase the volume of fluid imbibed into the core to enable the dosage form to dispense substantially all of the antihyperglycemic drug through the passageway and/or the porous membrane. In the latter situation, it may not be necessary to incorporate the laser drilled holes in the semipermeable membrane. The flux-enhancing agent can be a water-soluble material or an enteric material. Examples of the preferred materials that are useful as flux enhancers are sodium chloride, potassium chloride, sucrose, sorbitol, mannitol, polyethylene glycols (PEG), propylene glycol, hydroxypropyl cellulose, hydroxypropyl methylcellulose, hydroxypropyl methylcellulose phthalate, cellulose acetate phthalate, polyvinyl alcohols, methacrylic acid copolymers, poloxamers (such as LUTROL F68, LUTROL F127, LUTROL F108 which are commercially available from BASF) and mixtures thereof. A preferred flux-enhancer is PEG 400.

The flux enhancer may also be a drug that is water soluble such as metformin or its pharmaceutically acceptable salts, or the flux enhancer may be a drug that is soluble under intestinal conditions. If the flux enhancer is a drug, the present dosage form has the added advantage of providing an immediate release of the drug that has been selected as the flux enhancer.

The flux enhancing agent comprises approximately 0 to about 40% of the total weight of the coating, most preferably about 2% to about 20% of the total weight of the coating. The flux enhancing agent dissolves or leaches from the membrane or sustained release coating to form channels in the membrane or sustained release coating which enables fluid to enter the core and dissolve the active ingredient.

The membrane or sustained release coating may also be formed using a commonly known excipient such as a plasticizer. Some commonly known plasticizers include adipate, azelate, enzoate, citrate, stearate, isoebucate, sebacate, triethyl citrate, tri-n-butyl citrate, acetyl tri-n-butyl citrate, citric acid esters, and those described in the Encyclopedia of Polymer Science and Technology, Vol. 10 (1969), published by John Wiley & Sons. The preferred plasticizers are triacetin, polyethylene glycols (PEG) (i.e PEG 400, PEG 8000), acetylated monoglyceride, grape seed oil, olive oil, sesame oil, acetyltributylcitrate, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate and the like. Depending on the particular plasticizer, amounts from about 0 to about 25%, and preferably about 2% to about 15% of the plasticizer can be used based upon the total weight of the membrane or sustained release coating.

Generally, the membrane or sustained release coating around the core will comprise from about 1% to about 10% and preferably about 2% to about 5% based upon the total weight of the core and coating.

In a preferred embodiment, the membrane or sustained release coating surrounding the core further comprises a passageway that will allow for controlled release of the drug from the core. As used herein the term passageway includes an aperture, orifice, bore, hole, weakened area or an erodible element such as a gelatin plug that erodes to form an osmotic passageway for the release of the antihyperglycemic drug from the dosage form. Passageways used in accordance with the subject invention are well known and are described in U.S. Pat. Nos. 3,845,770; 3,916,899; 4,034,758; 4,077,407; 4,783,337 and 5,071,607.

Independent of the antihyperglycemic is a second active drug, preferably a thiazolidinedione derivative. This second active drug is formulated to provide an immediate release of the thiazolidinedione derivative. In one embodiment of the present invention the thiazolidinedione derivative is applied in the form of a layer to a controlled or sustained released core comprising the antihyperglycemic drug. The thiazolidinedone derivative layer employs a binder, a disintegrating agent and other conventional pharmaceutical excipients such as absorption enhancers, surfactants, plasticizers, antifoaming agents and combinations of the foregoing. An absorption enhancer may be present in the thiazolidinedione derivative layer in an amount up to about 30% w/w in comparison to the weight of the thiazolidinedione derivative. A binding agent may be present in an amount up to 150% w/w of the thiazolidinedione derivative.

In one embodiment the binder in the thiazolidinedione derivative layer is a water soluble binder, preferably a water soluble film forming binder, which has a low viscosity, typically less than 50 mPa·S, preferably less than 25 mPa·S, and most preferably less than 10 mPa·S, when tested as a 2% aqueous solution at 20° C. An example of such a water soluble binder is hydroxypropyl cellulose available from Nippon Soda Co., Ltd of Japan under the tradename HPC-SSL and HPC-SL which have a reported viscosity of 2-3 mPa·S and 3-6 mPa·S respectively. Other preferred binders include low molecular weight povidones, polyvinyl alcohols and hydroxypropyl methylcelluloses.

If a surfactant is employed in the thiazolidinedone derivative layer it is preferred that the surfactant be a non-ionic surfactant such as the polysorbates or polaxamers. If a surfactant is employed it should be about 0.5-40%, preferably about 1 to about 15% and most preferably about 5 to about 12% of the total weight of the thiazolidinedone derivative layer.

The disintegrating agent used in the thiazolidinedone derivative layer can be selected from the group consisting of corn starch, croscarmelose sodium, crospovidone (polyplasdone XL-10, sodium starch glycolate (EXPLOTAB or PRIMOJEL) or any combination of the foregoing. The most preferred disintegrating agent is crospovidone or sodium starch glycolate. The disintegrating agent should be present in the in about 1-40%, preferably about 5-30%, most preferably about 10-20% of the total weight of the thiazolidinedone derivative layer.

A second active drug immediate release formulation may be incorporated into a single dosage form by coating onto the membrane or sustained release coating of the dosage form by conventional methods. The incorporation of the second active drug may be performed by, but would not be limited to, the processes selected from the group consisting of drug layering, lamination, dry compression, deposition and printing.

When the thiazolidinedione derivative is coated onto a membrane or sustained release coating of an osmotic tablet core, the thiazolidinedione coating should be applied from a coating solution or suspension that employs an aqueous solvent, an organic solvent or a mixture of an aqueous and an organic solvent. Typical organic solvents include acetone, isopropyl alcohol, methanol and ethanol. If a mixture of aqueous and organic solvents is employed, the ratio of water to organic solvent should range from 98:2 to 2:98, preferably 50:50 to 2:98, most preferably 30:70 to 20:80 and ideally about 25:75 to 20:80. If a mixed solvent system is employed, the amount of binder required for coating the thiazolidinedione derivative onto the membrane or sustained release coating may be reduced. For example, successful coatings have been obtained from a mixed solvent system where the ratio of binder to thiazolidinedione derivative is 1:9 to 1:11. Although acceptable coatings can be obtained when the thiazolidinedione coat is applied directly to the membrane or sustained release coating, a preferred approach is to first coat the membrane or sustained release coating with a seal coat prior to the application of the thiazolidinedione coating. As used herein a seal coat is a coating that does not contain an active pharmaceutical ingredient and that rapidly disperses or dissolves in water. It may be necessary to apply about 5 to 20% excess, preferably about 10-15% excess of the thiazolidinedione coating solution to account for losses during the coating process.

The thiazolidinedione coating solution or suspension may also contain a pore forming agent. A pore forming is preferably a water-soluble material such as sodium chloride, potassium chloride, sucrose, lactose, sorbitol, mannitol, polyethylene glycols (PEG), propylene glycol, hydroxypropyl methylcellulose phthalate, cellulose acetate phthalate, and mixtures thereof. In an alternative embodiment, the dosage form of the present invention may also comprise an effective immediate release amount of the antihyperglycemic drug. The effective immediate release amount of antihyperglycemic drug may be coated onto the membrane or sustained release coating of the dosage form or it may be incorporated into the membrane or sustained release coating.

In addition, various diluents, excipients, lubricants, dyes, pigments, dispersants, etc., which are disclosed in Remington's Pharmaceutical Sciences (1995), may be used to optimize the above listed formulations of the subject invention.

Biguanides, such as metformin are commonly administered in dosage forms containing 500 mg, 750 mg, 850 mg, and 1000 mg. Thiazolidinedione derivatives, for example pioglitizone, are commonly administered in dosage forms containing 15 mg, 30 mg and 45 mg. The present invention is intended to encompass the above listed therapeutic combinations, without providing a specific example of each possible combination of compounds and their respective dosage amounts.

A preferred embodiment the dosage form will have the following composition:

| FIRST ACTIVE DRUG | |
| --- | --- |
| Core: | Amount (% of core) |
| drug | 50-98% (75-95% preferred) |
| binder | 0.1-40% (3-15% preferred) |
| absorption enhancer | 0-20% (2-10% preferred) |
| lubricant | 0-5% (0.5-1% preferred) |
| Coating: | Amount (% of coating) |
| polymer | 50-99% (75-95% preferred) |
| flux enhancer | 0-40% (2-20% preferred) |
| plasticizer | 0-25% (2-15% preferred) |

| SECOND ACTIVE DRUG | |
| --- | --- |
| | Amount (% of total dosage form) |
| drug | 0.1-20% (1-10% preferred) |
| binder | 0.1-30% (0.1-10% preferred) |
| disintegrating agent | 1.0-40% (1-10% preferred) |
| pore forming agent | 1.0-40% (2-10% preferred) |
| surfactant | 0.1-10% (0.5-5% preferred) |

The dosage forms prepared according to the present invention exhibit the following dissolution profile when tested in a USP Type 2 apparatus at 75 rpm in 900 ml of simulated intestinal fluid (pH 7.5 phosphate buffer) and at 37° C.:

| Release of First Active Drug | |
| --- | --- |
| Time (hours) | % release |
| 2 | 0-25% (0-20% preferred) |
| 4 | 10-45% (20-40% preferred) |
| 8 | 30-90% (45-90% preferred) |
| 12 | NLT 50% (NLT 60% preferred) |
| 16 | NLT 60% (NLT 70% preferred) |
| 20 | NLT 70% (NLT 80% preferred) |

NLT = NOT LESS THAN

| Release of Second Active Drug | |
| --- | --- |
| Time (hours) | % release |
| 0.5 | NLT 60% (NLT 80% preferred) |

It has been discovered that the selection of the excipients for use in the thiazolidinedione component of the dosage form can greatly affect the release characteristics, potency and stability of the thiazolidinedione. Therefore, in an alternate embodiment of the present invention, the composition of the thiazolidinedione component of the present invention should be selected so that not less than 85%, preferably not less than 90% and most preferably not less than 95% of the thiazolidinedione is released from the dosage form within 45 minutes, preferably within 40 minutes and most preferably within 30 minutes when tested according to the United States Pharmacopeia (USP) 26, with Apparatus 1 at 100 rpm, 37° C. and 900 ml of 0.3 M KCl—HCl Buffer, pH 2.0.

Further the excipients for use in the thiazolidinedione component of the dosage form should be selected so that the total thiazolidinedione related compounds or impurities in the final dosage form are not more than 0.6%, preferably not more than 0.5% and most preferably not more than 0.25% and each individual thiazolidinedione related compound or impurity in the final dosage form is not more than 0.25%, preferably not more than 0.2% and most preferably not more than 0.1%. The thiazolidinedione related compounds or impurities in the final dosage form are determined by High Performance Liquid Chromatography (HPLC) using a YMC-ODS-AQ, 5 µm, 120 Å, 4.6×250 mm or equivalent column, a 0.1 M ammonium acetate buffer:acetonitrile:glacial acetic acid (25:25:1) mobile phase, about a 40 µL injection volume, 0.7 mL/min flow rate, 25° C. column temperature and 269 nm wavelength for the UV detector.

In addition, the excipients for use in the thiazolidinedione derivative component of the dosage form should be selected so that the there is a significant increase in the bioavailability of the thiazolidinedione derivative component when compared to a conventional immediate release dosage form that contains only a thiazolidinedione derivative as the active ingredient. Although the following examples describe a dosage formulation that exhibits increased bioavailability for the thiazolidinedione derivative which employs a disintegrating agent in association with the thiazolidinedione derivative, this description of one embodiment is not intended to limit invention or the claims.

Accordingly, in certain preferred embodiments of the present invention there may be provided an immediate release thiazolidinedione derivative-containing tablet having the improved release characteristics described hereinabove, wherein the tablet comprises the thiazolidinedione derivative active in combination with a surfactant, and optionally in combination with other excipients, such as, but not limited to, a binder, a disintegrating agent and a pore forming agent. The immediate release thiazolidinedione derivative-containing tablets of the present invention are prepared by convention means, direct compression, wet granulation or dry granulation, and may be uncoated, or coated with a seal coating as described above. The proportions for theses ingredients are the same as set forth for the second active layer.

EXAMPLES

The following are provided by way of example only and are in no means intended to be limiting.

Reference Example 1

A controlled release tablet containing 850 mg of metformin HCl and 15 mg pioglitazone is prepared as follows:

| First Active Drug | | |
| --- | --- | --- |
| I. Core | | (% composition of core) |
| Metformin HCl | | 88.555% |
| Povidone K-90[3], USP | | 6.368% |
| Sodium Lauryl Sulfate | | 4.577% |
| Magnesium Stearate | | 0.5% |

[3]approximate molecular weight = 1,000,000, dynamic viscosity (10% w/v solution) 300-700 mPa·s at 20° C.

(a) Granulation

The metformin HCl and sodium lauryl sulfate are delumped by passing them through a 40 mesh screen and collecting them in a clean, polyethylene-lined container. The povidone, K-90, is dissolved in purified water. The delumped metformin HCl and sodium lauryl sulfate are then added to a top-spray fluidized bed granulator and granulated by spraying with the binding solution of povidone under the following conditions: inlet air temperature of 50-70° C.; atomization air pressure of 1-3 bars and spray rate of 10-100 ml/min.

Once the binding solution is depleted, the granules are dried in the granulator until the loss on drying is less than 2%. The dried granules are passed through a comil equipped with the equivalent of an 18 mesh screen.

(b) Tableting

The magnesium stearate is passed through a 40 mesh stainless steel screen and blended with the metformin HCl granules for approximately five (5) minutes. After blending, the granules are compressed on a rotary press fitted with 15/32" round standard concave punches (plain lower punch, upper punch with an approximately 1 mm indentation pin).

As stated above, the orifice may be formed by any means commonly employed in the pharmaceutical industry.

(c) Seal Coating (Optional)

The core tablet is seal coated with an Opadry material or other suitable water-soluble material by first dissolving the Opadry material, preferably Opadry Clear in purified water. The Opadry solution is then sprayed onto the core tablet using a pan coater under the following conditions: exhaust air temperature of 38-42° C.; atomization pressure of 28-40 psi and spray rate of 10-15 ml/min. The core tablet is coated with the sealing solution until a theoretical coating level of approximately 2% is obtained.

| II | Membrane | (% composition of membrane) |
|---|---|---|
| | Cellulose Acetate (398-10)[4] | 85% |
| | Triacetin | 5% |
| | PEG 400 | 10% |

[4] acetyl content 39.3-40.3%

(a) Membrane Coating Process

The cellulose acetate is dissolved in acetone while stirring with a homogenizer. The polyethylene glycol 400 and triacetin are added to the cellulose acetate solution and stirred. The coating solution is then sprayed onto the seal coated tablets in a fluidized bed coater employing the following conditions: product temperature of 16-22° C.; atomization pressure of approximately 3 bars and spray rate of 120-150 ml/min. The sealed core tablet is coated until a theoretical coating level of approximately 3% is obtained.

| III. | Second Active Drug Layering | (% composition of second component) |
|---|---|---|
| | Pioglitizone HCl | 43.5% |
| | Tween 80 | 2.0% |
| | Hydroxypropyl methylcellulose | 54.5% |

Tween 80 and hydroxypropyl methylcellulose are dissolved in purified water. Pioglitizone HCl is then dispersed into this solution. The resulting suspension is then sprayed onto the above described tablets.

Example 1

A controlled release tablet containing 500 mg of metformin HCl and 15 mg pioglitazone is prepared as follows:

I. First Active Drug

A 500 mg metformin membrane coated tablet is prepared as described in Comparative Example 1 above except that compound cup toolings are used during tableting. The 500 mg metformin membrane coated tablet has the following composition:

| CORE | |
|---|---|
| Metformin HCl | 500 mg/tablet |
| Povidone K-90, USP | 35.96 mg/tablet |
| Sodium lauryl sulfate, NF | 25.84 mg/tablet |
| Magnesium stearate, NF | 2.82 mg/tablet |
| SEAL COATING | |
| Opadry Clear (YS-1-7006) | 23.53 mg/tablet |
| MEMBRANE COATING | |
| Cellulose Acetate, 398-10, NF | 23.56 mg/tablet |
| Triacetin, USP | 1.39 mg/tablet |
| Polyethylene Glycol 400, NF | 2.77 mg/tablet |
| Total weight | 615.87 mg/tablet |

II. Second Active Drug Layering

An immediate release amount of pioglitiazone HCL is applied to the 500 mg metformin HCl membrane coated tablet prepared in step I. The final tablet has the following composition:

| Metformin HCl membrane coated | 615.87 mg/tablet |
|---|---|
| Pioglitazone Coating | |
| Pioglitazone HCl | 16.53 mg/tablet |
| Tween 80 | 2.0 mg/tablet |
| Polyplasdone XL | 15.0 mg/tablet |
| Opadry Clear (YS-1-7006) | 8.47 mg/tablet |
| Color Coating | |
| Opadry White | 10.0 mg/tablet |
| Polishing Coat | |
| Candelilla Wax Powder | 2.0 mg/tablet |

The pioglitazone coating is directly applied to the 500 mg metformin HCl membrane coated tablets. The pioglitazone coating is prepared by dissolving 0.252 kg of Opadry Clear, 0.269 kg of Polyplasdone XL and 0.036 kg of Tween 80 in 9.908 kg of purified water using a homogenizer. Once these ingredients are dissolved, 0.296 kg of pioglitazone HCl is dispersed into the solution and homogenized. The homogenized dispersion is then directly applied to the 500 mg metformin HCl membrane coated tablets using a 24" O'Hara Labcoat III pan coater with the following conditions:

| Spray Rate | 15-27 mL/min |
|---|---|
| Exhaust Temperature | 42-47° C. |
| Atomization Air Pressure | 25 psi |
| Pan Speed | 5-9 rpm |
| Inlet Air Flow | 300-400 CFM |

Once the pioglitazone coating has been applied to the 500 mg metformin HCl membrane coated tablet, an aesthetic or color coating of Opadry white is applied to the pioglitazone coated tablet. The color coating is prepared by dispersing 0.179 kg of Opadry White in 1.791 kg of purified water. The Opadry White suspension is applied to the pioglitazone coated tablet using a 24" O'Hara Labcoat III pan coater under the following conditions:

| Spray Rate | 20-35 mL/min |
|---|---|
| Exhaust Temperature | 35-45° C. |
| Atomization Air Pressure | 25 psi |
| Pan Speed | 9 rpm |
| Inlet Air Flow | 390-500 CFM |

Once the color coating is applied, the tablets are polished using 0.036 kg of Candelilla wax powder.

Reference Example 2

A controlled release tablet containing 1000 mg of metformin HCl and 30 mg pioglitazone is prepared as follows:

| I. First Active Drug | |
|---|---|
| A. Core | (% composition of core) |
| Metformin HCl | 88.07% |
| Povidone K-90[3], USP | 6.87% |
| Sodium Lauryl Sulfate | 4.55% |
| Magnesium Stearate | 0.5% |

[3]approximate molecular weight = 1,000,000, dynamic viscosity (10% w/v solution) 300-700 mPa · s at 20° C.

Approximately 206.34 kg of purified water is added to a stainless steel tank followed by approximately 10.86 kg of povidone K-90. The solution is mixed at about 330-360 rpms for about 45 minutes or until the povidone is completely dissolved. Approximately 139.14 kg of metformin HCl is passed through a Comil equipped with a #813 screen and no spacer at 840-850 rpms.

The screened metformin HCl is loaded into a GPCG-60 (Glatt) brand fluidized bed coater with Wurster insert (size 32" by 35 mm high) with 3 nozzles of size 1.5 mm. The metformin HCl is fluidized and the product temperature is adjusted to about 38-43° C. The povidone solution is sprayed onto the fluidized metformin HCl with an atomization pressure of about 2.5-3.0 bars and the pump rate of:

| 0-15 minutes | 491-515 g/min (target 500 g/min) |
|---|---|
| 16-30 minutes | 680-710 g/min (target 700 g/min) |
| 31-45 minutes | 860-910 g/min (target 900 g/min) |
| 46-60 minutes | 1090-1170 g/min (target 1100 g/min) |
| 61 minutes to end | 1170-1220 g/min (target 1200 g/min). |

Once the povidone solution has been consumed, the granules are dried in the fluidized bed at about 2100 CFM and 60° C. inlet air temperature until the loss on drying (LOD) is not more than 2%. The resulting granules are passed through a Comil equipped with a #1143 stainless steel screen and a #075 spacer at a speed of 1086-1088 rpms to produce approximately 150 kg of metformin HCl granules. The granulation process is repeated a second time to produce appromixately 300 kg of metformin HCl granules.

Approximately 300 kg of the metformin granules are added to a 50 cu. Ft. Slant-Cone blender along with approximately 14.38 kg of sodium lauryl sulfate and blended for about 20 minutes. About 1.58 kg of magnesium stearate is passed through a #40 mesh stainless steel screen then added to the mixture in the Slant-Cone blender. The resulting mixture is blended for about 5 minutes then compressed into tablets using a conventional tablet press equipped with a ½" round compound cup die, a pre-compression force of 6 and a main compression force of 38. The resulting tablets exhibit a weight range of 1044 g to about 1226 g with a target weight of 1135 g, hardness of 20-36 kp (target of 28 kp) and a friability of less than or equal to 0.8%

B. Seal Coating

About 57.61 kg of the core tablets prepared above are seal coated with an Opadry material or other suitable water-soluble material by first dissolving the Opadry material, preferably about 3.98 kg of Opadry Clear (YS-1-7006), in about 21.49 kg of purified water. The Opadry solution is then sprayed onto the core tablet using an O'Hara Labcoat III pan coater with a 36" pan, 3 spray guns under the following conditions: exhaust air temperature of 40-47° C.; atomization pressure of 50±10 psi, and spray rate of 180±60 g/min/3 guns, pan speed of 4-8 rpms and air volume of 1000±200 CFM. The core tablet is coated with the sealing solution until a theoretical coating level of approximately 2.8-4.4% is obtained.

C. Membrane Coating

A cellulose acetate membrane coating is applied to the seal coated metformin HCl tablet cores to produce membrane coated metformin HCl tablets with the following composition:

| Metformin HCl 1000 mg Tablet | 98.456% |
|---|---|
| Cellulose Acetate (398-10)[4] | 1.313% |
| Triacetin | 0.077% |
| PEG 400 | 1.54% |

[4]acetyl content 39.3-40.3%

Approximately 29.95 kg of acetone is added to a stainless steel tank followed by about 0.788 kg of cellulose acetate and mixed for about 20 minutes until the solution becomes clear. Once the solution is clear about 0.092 kg of polyethylene glycol 400 is added to the solution and mixed for about 5 minutes followed by the addition of about 0.046 kg of triacetin. The solution is mixed for an additional 5 minutes.

About 59.07 kg of the seal coated metformin HCl tablets are loaded into a GPCG-60 (Glatt) brand fluidized bed coater with Wurster insert (size 18" by 45 mm high) with a nozzle of size 1.5 mm. The seal coated metformin HCL tablets are fluidized and the product temperature is adjusted to about 21±3° C. The cellulose acetate solution is sprayed onto the fluidized seal coated metformin HCL tablets with an atomization pressure of about 2.0-3.0 bars, air volume of 1600±300 CFM and a spray rate of 400±100 g/min until a weight gain of 1-2% (target 1.38%) is obtained. Once the desired amount of membrane coating has been applied the membrane coated tablets are dried in the fluidized bed 21±3° C. and 1350±100 CFM for about 10 minutes followed by 40° C. and 1350±100 CFM for about 5 minutes.

The resulting membrane coated tablets are laser drilled to create an orifice in the approximate center of each side of the membrane coated tablet (i.e 2 orifices) with an average diameter of 0.5 mm per orifice. The top micrometer is 6.5±2 mm, bottom micrometer is 6.75±2 mm, the pulse width of the laser is 170±70 and pulse delay of 340±150 and 350±150 respectively.

II. Second Active Drug

An immediate release amount of pioglitazone HCL is applied to the 1000 mg metformin HCl membrane coated tablets prepared in step I. The final tablet has the following composition:

| | |
|---|---|
| Metformin HCl membrane coated tablet | 1201.0 mg/tablet |
| Seal Coat | |
| Opadry Clear (YS-1-7006) | 9.00 mg/tablet |
| Pioglitazone Coating | |
| Pioglitazone HCl | 33.06 mg/tablet |
| Hydroxypropyl Cellulose, NF (HPC-SSL) | 9.0 mg/tablet |
| Lactose Monohydrate, NF (modified spray dried) | 30.0 mg/tablet |
| Polyethylene Glycol 8000, NF | 0.450 mg/tablet |
| Titanium Dioxide, USP | 0.90 mg/tablet |
| Polishing Coat | |
| Candelilla Wax Powder | 0.40 mg/tablet |

The seal coat was applied to approximately 12.09 kg of the 1000 mg metformin HCl membrane coated tablet prepared in step A described above. The seal coating was prepared by dispersing about 0.91 kg of Opadry Clear (YS-1-7006) in about 1.133 kg of purified water for 30 minutes. The dispersion was sprayed onto approximately 12.09 kg of the 1000 mg metformin HCl tablet cores using a 24" O'Hara Labcoat III pan coater with the nozzle tip set 4±2" from the top of the static bed, 3 spray guns and the following conditions:

| | |
|---|---|
| Spray Rate | 20 ± 10 mL/gun/min |
| Exhaust Temperature | 40° C. ± 5° C. |
| Atomization Air Pressure | 10-40 psi |
| Pan Speed | 4-9 rpm |
| Supply Air Flow | 300 ± 100 CFM |
| Pattern Air Pressure | 10-40 psi |

The pioglitazone coating was applied to the seal coated 1000 mg metformin HCl membrane coated tablets. The pioglitazone coating was prepared by slowly dispersing about 0.104 kg of hydroxypropyl cellulose, NF (HPC-SLL) in about 8.499 kg of purified water. The HPC-SSL and water was mixed for about 20 minutes, then 0.347 kg of lactose monohydrate, NF (modified spray dried) was added to the HPC-SSL/water mixture and mixed for about 2 minutes. After the lactose was mixed in, approximately 0.005 kg of polyethylene glycol 8000 NF and 0.010 kg of titanium dioxide, USP were added to the water, HPC-SSL and lactose mixture and mixed for about 5 minutes. After about 5 minutes of mixing about 0.383 kg pioglitazone hydrochloride was dispersed into the coating solution. This coating solution contained approximately 15% excess material to compensate for material loss during the coating process. The pioglitazone suspension was stirred until the suspension was consumed during the coating process. The pioglitazone HCl suspension was applied to the seal coated 1000 mg metformin HCl membrane coated tablet cores using a 24" O'Hara Labcoat III pan coater with the nozzle tip set 4±2" above the top of the static bed, 3 spray guns with the following conditions:

| | |
|---|---|
| Spray Rate | 20 ± 10 mL/gun/min |
| Exhaust Temperature | 40 ± 5° C. |
| Atomization Air Pressure | 10-40 psi |
| Pan Speed | 4-9 rpms |
| Pattern Air Pressure | 10-40 psi |
| Supply Air Flow | 300 ± 100 CFM |

Once the pioglitazone tablets were dried, the exhaust air was turned off and the pan speed was adjusted to about 3-4 rpms and 0.004 kg of Candellia wax powder that had been passed through a 60 mesh screen was sprinkled onto the tablets. After the tablets have rolled in the wax for about 5 minutes the exhaust air was turned on and the tablets were rolled for an additional 10 minutes.

The finished polished tablet released greater than 95%@30 minutes of the pioglitazone when tested in a USP apparatus type 1 at 100 rpm in a pH 2.0 HCl-0.3M KCl buffer solution. The final tablets also exhibited a hardness greater than 35 kp and a friability of 0.00%. The final tablet was tested for pioglitazone related compounds by HPLC using a YMC-ODS-AQ, 5 µm, 120 Å, 4.6×250 mm column, a 0.1 M ammonium acetate buffer:acetonitrile:glacial acetic acid (25:25:1) mobile phase, a 40 µL injection volume, 0.7 mL/min flow rate, 25° C. column temperature and 269 nm wavelength for the UV dectector. The results of the test are reported in Table 1 below.

The final polished tablet was packaged in a 100 cc HDPE bottle containing one (1) 3 g SORB-IT® desiccant canister and subjected to accelerated stability conditions of 40° C. and 75% relative humidity for fifteen days, 1 month 2 months, 3 months and 6 months. After storage, the final polished tablet was tested and found to contain the following pioglitazone related compounds when tested by HPLC using a YMC-ODS-AQ, 5 µm, 120 Å, 4.6×250 mm column, a 0.1 M ammonium acetate buffer:acetonitrile:glacial acetic acid (25:25:1) mobile phase, a 40 µL injection volume, 0.7 mL/min flow rate, 25° C. column temperature and 269 nm wavelength for the UV dectector.

TABLE 1

| Name | Initial (%) | 0.5 M (%) | 1M (%) | 2 M (%) | 3M (%) | 6M (%) |
|---|---|---|---|---|---|---|
| RS-1 | 0.01 | 0.01 | 0.01 | N.D. | N.D. | N.D. |
| RS-2 | 0.02 | 0.03 | 0.03 | 0.02 | 0.03 | 0.02 |
| RS-3 | 0.03 | 0.04 | 0.03 | 0.03 | 0.04 | 0.04 |
| RS-4 | 0.03 | 0.02 | 0.03 | 0.03 | 0.02 | 0.02 |
| RS-5 | 0.04 | 0.04 | 0.04 | 0.04 | 0.03 | 0.04 |

"M" = months
"N.D." = none detected
RS-1 is (+/−)-5-[p-[2-(5-ethyl-2-pyridyl)ethoxy]benzyl]-5-hydroxy-2,4-thiazolidinedione
RS-2 is (z)-5-[p-[2-(5-ethyl-2-pyridyl)ethoxy]benzylidene]-2,4-thiazolidindione.
RS-3 is (+/−)-5-[p-[2-(5-ethyl-2-pyridyl)ethoxy]benzyl]-3-2[2-(5-ethyl-2-pyridyl)ethyl]-2,4-thiazolidindione.
RS-4 is (+/−)-ethyl-2-carbomoyltio-3-[4-[2-(5-ethyl-2-pyridyl)ethoxy]phenyl-]propionate.
RS-5 is ethyl-3-p-[2-(5-ethyl-2-pyridyl)ethoxy]phenyl-propionate.

Reference Example 3

A controlled release tablet containing 1000 mg of metformin HCl and 30 mg pioglitazone was prepared as follows:
A. First Active Drug Core
A cellulose acetate coated metformin HCl tablet core was prepared according to the procedure described in Reference Example 2.
B. Second Active Drug
An immediate release amount of pioglitazone HCL was applied to the 1000 mg metformin HCl membrane coated tablets prepared above in step A. The final tablet had the following composition:

| | |
|---|---|
| Metformin HCl membrane coated tablet | 1201.0 mg/tablet |
| Seal Coat | |
| Opadry Clear (YS-1-7006) | 9.00 mg/tablet |

-continued

| Pioglitazone Coating | |
| --- | --- |
| Pioglitazone HCl | 33.06 mg/tablet |
| Hydroxypropyl Cellulose, NF (HPC-SSL) | 9.0 mg/tablet |
| Lactose Monohydrate, NF (modified spray dried) | 30.0 mg/tablet |
| Polyethylene Glycol 8000, NF | 0.450 mg/tablet |
| Titanium Dioxide, USP | 0.90 mg/tablet |
| Color Coating | |
| Hydroxypropyl Cellulose (HPC-SSL) | 5.5 mg/tablet |
| Polyethylene Glycol 8000, NF | 1.38 mg/tablet |
| Titanium Dioxide, USP | 0.60 mg/tablet |
| Polishing Coat | |
| Candelilla Wax Powder | 0.40 mg/tablet |

The seal coat was applied to approximately 13.02 kg of the 1000 mg metformin HCl membrane coated tablet prepared in step A described above. The seal coating was prepared by dispersing about 0.098 kg of Opadry Clear (YS-1-7006) in about 1.220 kg of purified water for 30 minutes. The dispersion was then sprayed onto approximately 13.02 kg of the 1000 mg metformin HCl tablet cores using a 24" O'Hara Labcoat III pan coater with the nozzle tip set 4±2" from the top of the static bed, 3 spray guns and the following conditions:

| Spray Rate | 20 ± 10 mL/gun/min |
| --- | --- |
| Exhaust Temperature | 40° C. ± 5° C. |
| Atomization Air Pressure | 10-40 psi |
| Pan Speed | 4-9 rpm |
| Supply Air Flow | 300 ± 100 CFM |
| Pattern Air Pressure | 10-40 psi |

The pioglitazone coating then was applied to the seal coated 1000 mg metformin HCl membrane coated tablets. The pioglitazone coating was prepared by slowly dispersing about 0.108 kg of hydroxypropyl cellulose (HPC-SLL) in about 8.753 kg of purified water. The HPC-SSL and water was mixed for about 20 minutes, after which 0.358 kg of lactose monohydrate, NF (modified spray dried) was added to the HPC-SSL/water mixture and mixed for about 2 minutes. After the lactose was mixed in, approximately 0.006 kg of polyethylene glycol 8000 NF and 0.011 kg of titanium dioxide, USP were added to the water, HPC-SSL and lactose mixture and mixed for about 5 minutes. After about 5 minutes of mixing about 0.394 kg pioglitazone hydrochloride was dispersed into the coating solution. This coating solution contained approximately 10% excess material to compensate for material loss during the coating process. The pioglitazone suspension was stirred until the suspension was consumed during the coating process. The pioglitazone HCl suspension was applied to the seal coated 1000 mg metformin HCl membrane coated tablet cores using a 24" O'Hara Labcoat III pan coater with the nozzle tip set 4±2" above the top of the static bed, 3 spray guns, with the following conditions:

| Spray Rate | 20 ± 10 mL/gun/min |
| --- | --- |
| Exhaust Temperature | 40 ± 5° C. |
| Atomization Air Pressure | 10-40 psi |
| Pan Speed | 4-9 rpms |
| Pattern Air Pressure | 10-40 psi |
| Supply Air Flow | 300 ± 100 CFM |

Once the pioglitazone coating was applied to the seal coated 1000 mg metformin HCl membrane coated tablets, a color or aesthetic coating was applied to the pioglitazone coated tablet. The color coating was prepared by dispersing about 0.060 kg of HPC-SSL, 0.015 kg of polyethylene glycol 8000, NF and 0.007 kg of titanium dioxide, USP in 0.810 kg of purified water and mixing the dispersion for about 30 minutes. The color coating was then sprayed onto the pioglitazone HCl coated tablets using a 24" O'Hara Labcoat III pan coater with the nozzle tip set at 4±2" from the top of the static bed, 3 spray guns and the following conditions:

| Spray Rate | 20 ± 10 mL/gun/min |
| --- | --- |
| Exhaust Temperature | 40° C. ± 5° C. |
| Atomization Air Pressure | 10-40 psi |
| Pan Speed | 4-9 rpm |
| Supply Air Flow | 300 ± 100 CFM |
| Pattern Air Pressure | 10-40 psi |

The color coating dispersion was continuously stirred until the dispersion was consumed during the coating process.

Once the color coating suspension was consumed, the tablets were dried in the coating pan for about 5 minutes with a pan speed of about 2-8 rpms and an exhaust temperature of 40±5° C. Once the tablets were dried, the exhaust air is turned off and the pan speed is adjusted to about 3-4 rpms and 0.004 kg of Candellia wax powder that had been passed through a 60 mesh screen was sprinkled onto the tablets. After the tablets were rolled in the wax for about 5 minutes the exhaust air was turned on and the tablets were rolled for an additional 10 minutes.

The finished polished tablet released greater than 90% of the pioglitazone when tested in a USP apparatus type 1 at 100 rpm in a pH 2.0 HCl-0.3M KCl buffer solution. The average of the 12 vessel tested was 96% released. The final tablets also exhibited a hardness greater than 35 kp and a friability of 0.1%. The final tablet was tested for pioglitazone related compounds by HPLC using a YMC-ODS-AQ, 5 μm, 120 Å, 4.6×250 mm column, a 0.1 M ammonium acetate buffer:acetonitrile:glacial acetic acid (25:25:1) mobile phase, a 40 μL injection volume, 0.7 mL/min flow rate, 25° C. column temperature and 269 nm wavelength for the UV detector. The results of the test are reported in Table 2 below.

The final polished tablet was packaged in a 100 cc HDPE bottle containing one (1) 3 g SORB-IT® desiccant canister and subjected to accelerated stability conditions of 40° C. and 75% relative humidity for fifteen days, 1 month, 2 months, 3 months and 6 months. After storage, the final polished tablet was tested and found to contain the following pioglitazone related compounds when tested by HPLC using a YMC-ODS-AQ, 5 μm, 120 Å, 4.6×250 mm column, a 0.1 M ammonium acetate buffer:acetonitrile:glacial acetic acid (25:25:1) mobile phase, a 40 μL injection volume, 0.7 mL/min flow rate, 25° C. column temperature and 269 nm wavelength for the UV detector.

TABLE 2

| Name | Initial (%) | 0.5 M (%) | 1M (%) | 2 M (%) | 3M (%) | 6M (%) |
| --- | --- | --- | --- | --- | --- | --- |
| RS-1 | 0.01 | 0.01 | 0.01 | N.D. | N.D. | N.D. |
| RS-2 | 0.02 | 0.03 | 0.03 | 0.02 | 0.03 | 0.03 |
| RS-3 | 0.03 | 0.03 | 0.03 | 0.03 | 0.04 | 0.04 |
| RS-4 | 0.02 | 0.02 | 0.03 | 0.02 | 0.02 | 0.01 |
| RS-5 | 0.04 | 0.04 | 0.03 | 0.04 | 0.04 | 0.04 |

Example 2

A controlled release tablet containing 1000 mg of metformin HCl and 30 mg pioglitazone was prepared as follows:

A. First Active Drug Core

A cellulose acetate coated metformin HCl tablet core was prepared according to the procedure described in Reference Example 2.

B. Second Active Drug

An immediate release amount of pioglitazone HCL was applied to the 1000 mg metformin HCl membrane coated tablets prepared above in step A. The final tablet had the following composition:

| | |
|---|---|
| Metformin HCl membrane coated tablet | 1201.0 mg/tablet |
| Seal Coat | |
| Opadry Clear (YS-1-7006) | 9.00 mg/tablet |
| Pioglitazone Coating | |
| Pioglitazone HCl | 33.06 mg/tablet |
| Povidone, USP (Kollidon K-30) | 3.0 mg/tablet |
| Lactose Monohydrate, NF (modified spray dried) | 90.0 mg/tablet |
| Sodium Starch Glycolate pH 5.5-7.5, NF (EXPLOTAB) | 30.0 mg/tablet |
| Poloxamer 188, NF (LUTROL F-68) | 15.0 mg/tablet |
| Color Coating | |
| Hydroxypropyl Cellulose (HPC-SSL) | 5.32 mg/tablet |
| Polyethylene Glycol 8000, NF | 0.84 mg/tablet |
| Titanium Dioxide, USP | 0.84 mg/tablet |
| Polishing Coat | |
| Candelilla Wax Powder | 0.40 mg/tablet |

The seal coat was applied to approximately 12.11 kg of the 1000 mg metformin HCl membrane coated tablet prepared in step A described above. The seal coating was prepared by dispersing about 0.091 kg of Opadry Clear (YS-1-7006) in about 1.134 kg of purified water for 30 minutes. The dispersion was then sprayed onto approximately 12.11 kg of the 1000 mg metformin HCl tablet cores using a 24" O'Hara Labcoat III pan coater with the nozzle tip set 4±2" from the top of the static bed, 3 spray guns and the following conditions:

| | |
|---|---|
| Spray Rate | 20 ± 10 mL/gun/min |
| Exhaust Temperature | 40° C. ± 5° C. |
| Atomization Air Pressure | 10-40 psi |
| Pan Speed | 4-9 rpm |
| Supply Air Flow | 300 ± 100 CFM |
| Pattern Air Pressure | 10-40 psi |

The pioglitazone coating then was applied to the seal coated 1000 mg metformin HCl membrane coated tablets. The pioglitazone coating was prepared by slowly dissolving about 0.227 kg of Lutrol F-68 in about 2.0 kg of purified water. In a separate container about 0.045 kg of Kollidon K-30 was dissolved in about 14.25 kg of purified water and mixed for about 10 minutes. About 1.361 kg of lactose monohydrate, NF (modified spray dried) was added to the Kollidon solution and mixed for about 5 minutes. After the lactose was mixed in, the Lutrol F-68 solution was added and mixed for about 5 minutes. After mixing about 0.50 kg pioglitazone hydrochloride was dispersed into the coating suspension and mixed for about 10 minutes. Finally, about 0.453 kg of the sodium starch glycolate is added to the coating suspension and mixed for about 1 minute. This coating solution contained approximately 15% excess material to compensate for material loss during the coating process. The pioglitazone suspension was stirred until the suspension was consumed during the coating process. The pioglitazone HCl suspension was applied to the seal coated 1000 mg metformin HCl membrane coated tablet cores using a 24" O'Hara Labcoat III pan coater with the nozzle tip set 4±2" above the top of the static bed, 3 spray guns, with the following conditions:

| | |
|---|---|
| Spray Rate | 20 ± 10 mL/gun/min |
| Exhaust Temperature | 40 ± 5° C. |
| Atomization Air Pressure | 10-40 psi |
| Pan Speed | 4-9 rpms |
| Pattern Air Pressure | 10-40 psi |
| Supply Air Flow | 300 ± 100 CFM |

Once the pioglitazone coating was applied to the seal coated 1000 mg metformin HCl membrane coated tablets, a color or aesthetic coating was applied to the pioglitazone coated tablet. The color coating was prepared by dispersing about 0.054 kg of HPC-SSL, 0.008 kg of polyethylene glycol 8000, NF and 0.008 kg of titanium dioxide, USP in about 0.706 kg of purified water and mixing the dispersion for about 30 minutes. The color coating was then sprayed onto the pioglitazone HCl coated tablets using a 24" O'Hara Labcoat III pan coater with the nozzle tip set at 4±2" from the top of the static bed, 3 spray guns and the following conditions:

| | |
|---|---|
| Spray Rate | 20 ± 10 mL/gun/min |
| Exhaust Temperature | 40° C. ± 5° C. |
| Atomization Air Pressure | 10-40 psi |
| Pan Speed | 4-9 rpm |
| Supply Air Flow | 300 ± 100 CFM |
| Pattern Air Pressure | 10-40 psi |

The color coating dispersion was continuously stirred until the dispersion was consumed during the coating process.

Once the color coating suspension was consumed, the tablets were dried in the coating pan for about 5 minutes with a pan speed of about 2-8 rpms and an exhaust temperature of 40±5° C. Once the tablets were dried, the exhaust air is turned off and the pan speed is adjusted to about 3-4 rpms and 0.004 kg of Candellia wax powder that had been passed through a 60 mesh screen was sprinkled onto the tablets. After the tablets were rolled in the wax for about 5 minutes the exhaust air was turned on and the tablets were rolled for an additional 10 minutes.

The finished polished tablet released greater than 95% of the pioglitazone when tested in a USP apparatus type 1 at 100 rpm in a pH 2.0 HCl-0.3M KCl buffer solution. The final tablets also exhibited a hardness greater than 35 kp and a friability of 0.1%. The final tablet was tested for pioglitazone related compounds by HPLC using a YMC-ODS-AQ, 5 μm, 120 Å, 4.6×250 mm column, a 0.1 M ammonium acetate buffer:acetonitrile:glacial acetic acid (25:25:1) mobile phase, a 40 μL injection volume, 0.7 mL/min flow rate, 25° C. column temperature and 269 nm wavelength for the UV dectector. The results of the test are reported in Table 3 below.

The final polished tablet was packaged in a 100 cc HDPE bottle containing one (1) 3 g SORB-IT® desiccant canister and subjected to accelerated stability conditions of 40° C. and 75% relative humidity for fifteen days. After storage, the final polished tablet was tested and found to contain the following pioglitazone related compounds when tested by HPLC using a YMC-ODS-AQ, 5 μm, 120 Å, 4.6×250 mm column, a 0.1 M ammonium acetate buffer:acetonitrile:glacial acetic acid (25:25:1) mobile phase, a 40 μL injection volume, 0.7 mL/min flow rate, 25° C. column temperature and 269 nm wavelength for the UV dectector.

TABLE 3

| Name | Relative Retention Time | Initial Amount(%) | 0.5 Months Amount (%) |
|---|---|---|---|
| RS-1 | 0.7 | N.D* | 0.01. |
| Pioglitazone | 1.0 | | |
| RS-2 | 1.5 | 0.03 | 0.02 |
| RS-3 | 3.4 | 0.04 | 0.03 |
| RS-4 | 1.2 | 0.03 | 0.04 |
| RS-5 | 2.8 | 0.03 | 0.03 |

The dosage formulation described above in Example 2 was tested in vivo in a two way cross over study with the dosage formulations described in Reference Examples 2 and 3 and a combination of a ACTOS® (a commercially available immediate release 30 mg pioglitazone dosage formulation) and FORTAMET XT® (a commercially available controlled release 1000 mg metformin HCl tablet that is similar to the metformin HCl core tablet described in Reference Example 2 except it further contains an aesthetic or final color coating.) The in vivo test employed eleven subjects (originally 12 but one patient discontinued the study) and the patients were dosed shortly after the evening meal.

The $C_{max}$ and AUC (inf) for the pioglitazone component of the in vivo study was as follows:

| Product | $C_{max}$ | AUC (inf) |
|---|---|---|
| Reference Example 2 | 927 ng/ml | 9,727 ng * hr/ml |
| Reference Example 3 | 829 ng/ml | 9,848 ng * hr/ml |
| Example 2 | 1,339 ng/ml | 13,087 ng * hr/ml |
| ACTOS® | 947 ng/ml | 10,342 ng * hr/ml |

The $C_{max}$ and AUC (inf) for the metformin component of the in vivo study was as follows:

| Product | $C_{max}$ | AUC (inf) |
|---|---|---|
| Reference Example 2 | 1,301 ng/ml | 12,033 ng * hr/ml |
| Reference Example 3 | 1,457 ng/ml | 13,493 ng * hr/ml |
| Example 2 | 1,353 ng/ml | 12,345 ng * hr/ml |
| FORTAMET XT® | 1,421 ng/ml | 13,037 ng * hr/ml |

A statistical analysis of the serum pharmacokinetic parameters of the pioglitazone component of the in vivo study was as follows:

| Parameter | Treatment | LS Mean | Test/Reference | LS Mean Ratio |
|---|---|---|---|---|
| AUC (0-tlqc) | A | 9304 | A/D | 95.30 |
| | B | 9451 | B/D | 96.80 |
| | C | 12617 | C/D | 129.23 |
| | D | 9763 | | |
| AUC (0-inf) | A | 9727 | A/D | 94.05 |
| | B | 9848 | B/D | 95.23 |
| | C | 13087 | C/D | 126.55 |
| | D | 10342 | | |
| $C_{max}$ | A | 927.6 | A/D | 97.96 |
| | B | 891.9 | B/D | 94.19 |
| | C | 1339.2 | C/D | 141.43 |
| | D | 946.9 | | |

Treatment A = Reference Example 2
Treatment B = Reference Example 3
Treatment C = Example 2
Treatment D = 30 mg ACTOS® of (ACTOS/FORTAMET XT® combination)

A statistical analysis of the serum pharmacokinetic parameters of the metformin component of the in vivo study was as follows:

| Parameter | Treatment | LS Mean | Test/Reference | LS Mean Ratio |
|---|---|---|---|---|
| AUC (0-tlqc) | A | 11535 | A/D | 90.34 |
| | B | 13205 | B/D | 103.42 |
| | C | 11985 | C/D | 93.86 |
| | D | 12768 | | |
| AUC (0-inf) | A | 12033 | A/D | 92.30 |
| | B | 13493 | B/D | 103.50 |
| | C | 12345 | C/D | 94.70 |
| | D | 13037 | | |
| $C_{max}$ | A | 1301.3 | A/D | 91.54 |
| | B | 1457.3 | B/D | 102.52 |
| | C | 1353.4 | C/D | 95.21 |
| | D | 1421.5 | | |

Treatment A = Reference Example 2
Treatment B = Reference Example 3
Treatment C = Example 2
Treatment D = 30 mg ACTOS® of (ACTOS/FORTAMET XT® combination)

Figure 3:
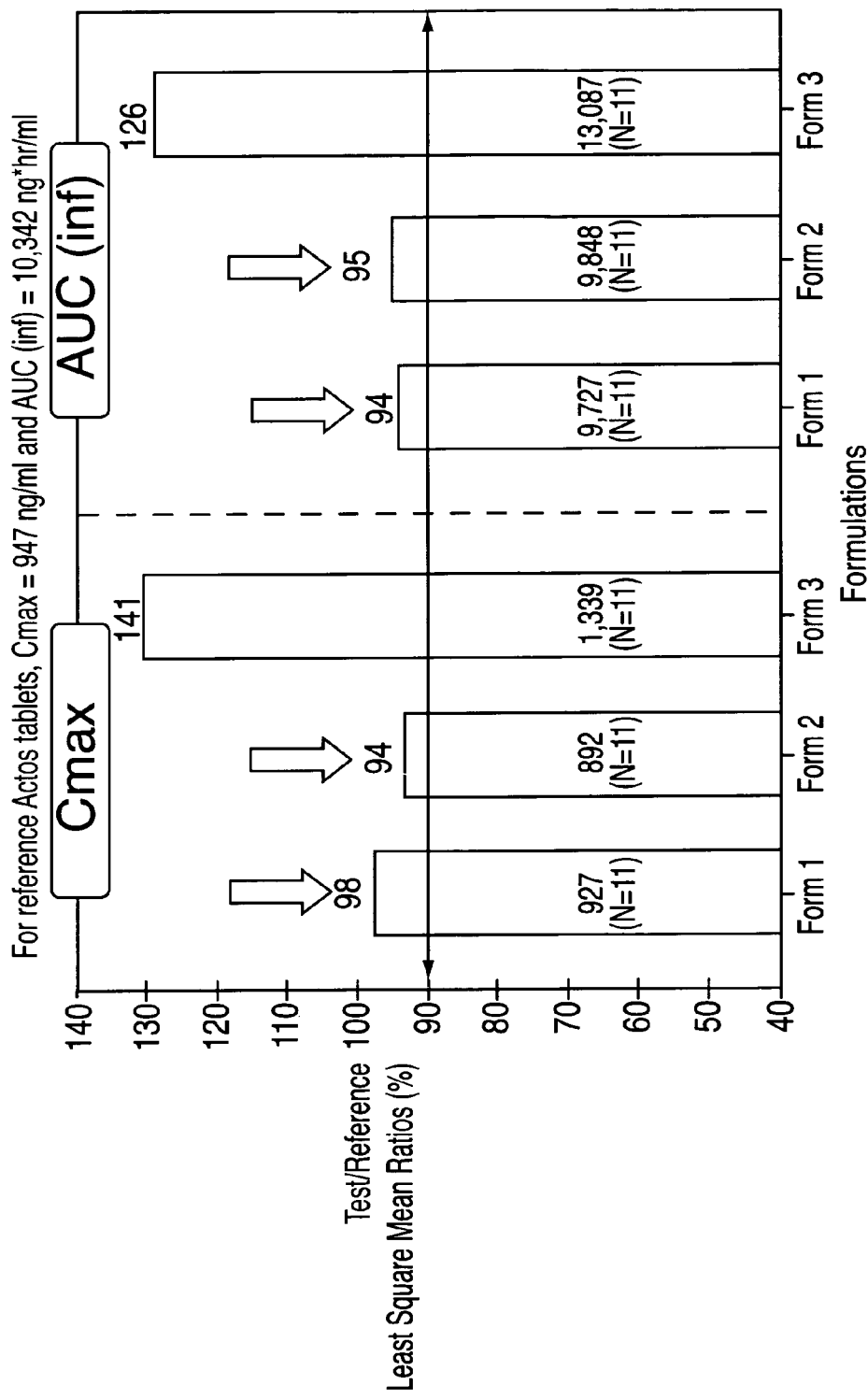
FIG. 3 is a graph depicting the pioglitazone Least Square Mean Ratio $C_{max}$ and AUC of the dosage formulation prepared in Example 2 compared with two reference formulations.

A graph depicting the mean pioglitazone serum concentration over time of the four treatments tested in the in vivo study is shown in FIG. 1 and a graph depicting the pioglitazone Least Square Mean Ratios of the four treatments tested in the in vivo study is shown in FIG. 3.

Figure 2:
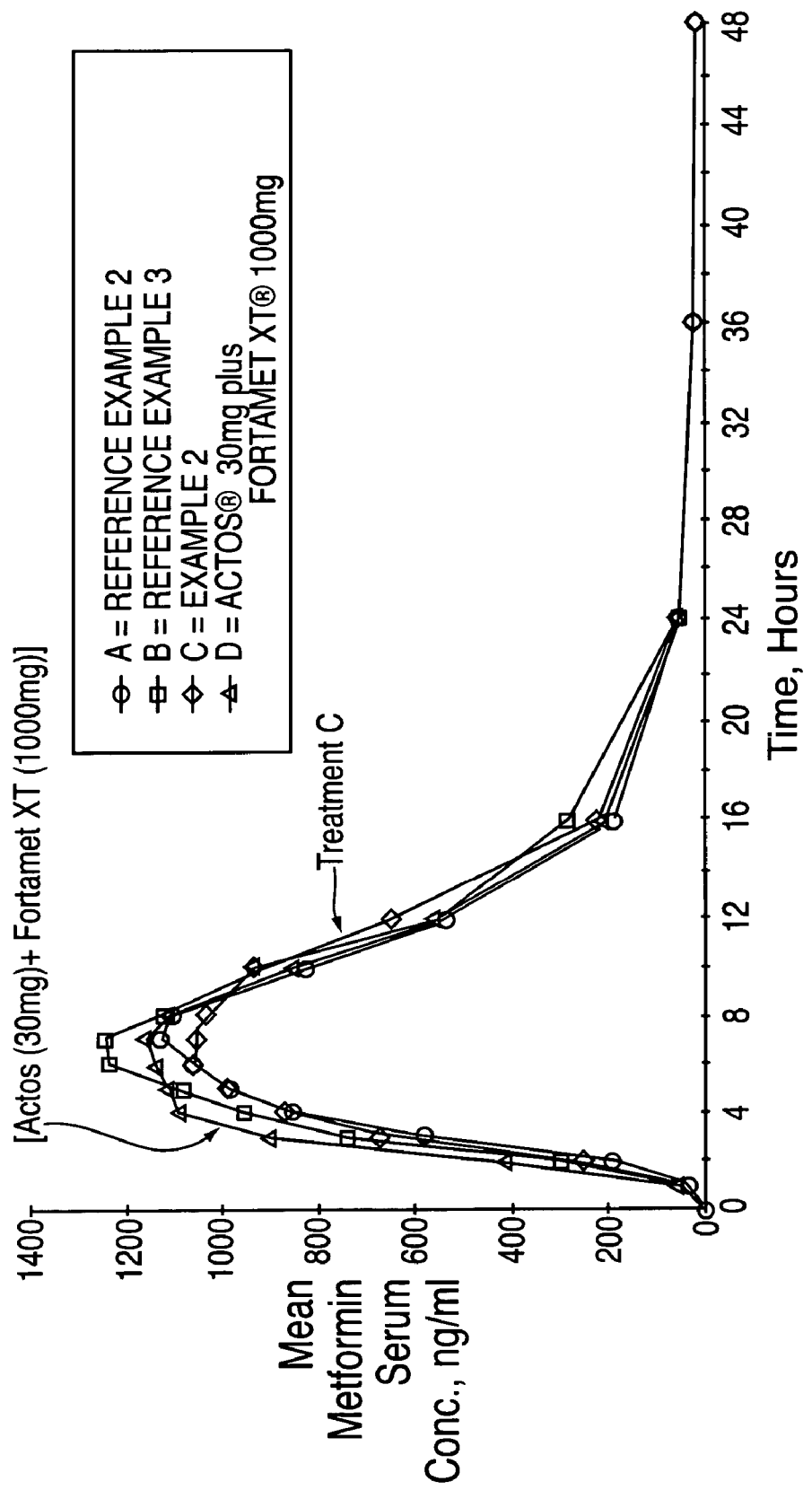
FIG. 2 is graph depicting the mean metformin serum concentration over time of the dosage formulation prepared in Example 2 compared to three reference formulations.
Figure 4:
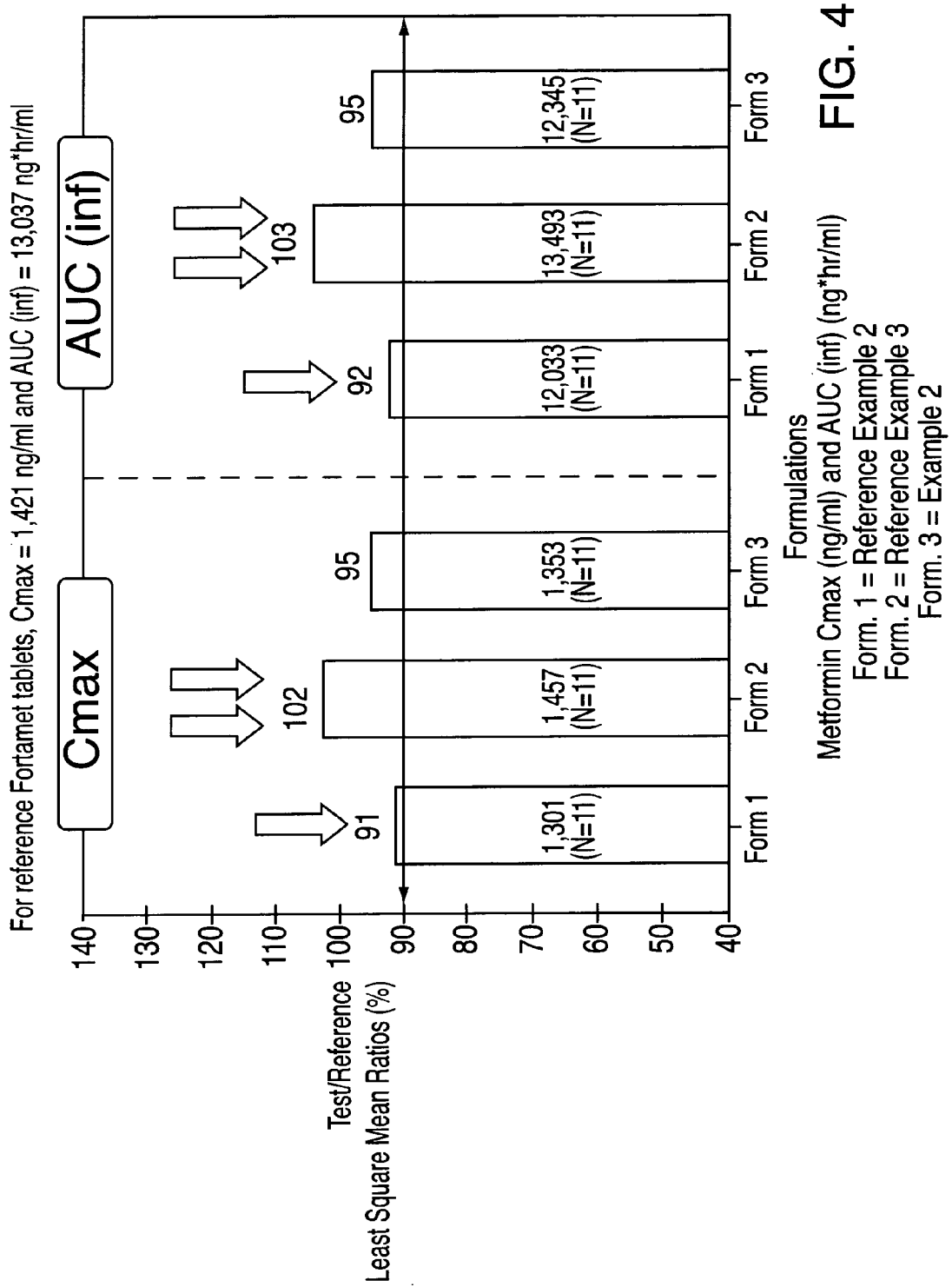
FIG. 4 is a graph depicting the metformin Least Square Mean Ratio $C_{max}$ and AUC of the dosage formulation prepared in Example 2 compared with two reference formulations.

A graph depicting the mean metformin serum concentration over time of the four treatments tested in the in vivo study is shown in FIG. 2 and a graph depicting the metformin Least Square Mean Ratios of the four treatments tested in the in vivo study is shown in FIG. 4.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

What is claimed is:

1. A pharmaceutical dosage form comprising:
   (a) a controlled release core comprising metformin hydrochloride and at least one pharmaceutically acceptable excipient; and
   (b) an immediate release pioglitazone layer applied to the controlled release metformin core wherein the immediate release pioglitazone layer comprises:
   (i) pioglitazone hydrochloride;
   (ii) a binder;
   (iii) about 1 to about 15% based upon the total weight of the pioglitazone layer of a poloxamer; and
   (iv) about 5 to about 30% based upon the total weight of the pioglitazone layer of sodium starch glycolate; and wherein not less than 95% of the pioglitazone is released from the dosage form within 30 minutes when tested according to the United States Pharmacopeia (USP) 26, with Apparatus 1 at 100 rpm, 37° C. and 900 ml of 0.3 M KCl—HCl Buffer, pH 2.0; and wherein the dosage form exhibits a $C_{max}$ for the pioglitazone that is at least 130% of the $C_{max}$ for an immediate release pioglitazone tablet containing the same amount of pioglitazone as present in the immediate release pioglitazone layer, and an AUC for the pioglitazone that is at least 115% of the AUC for the immediate release pioglitazone tablet.

2. The pharmaceutical dosage form as defined in claim 1 wherein the poloxamer comprises about 5 to about 12% of the total weight of the pioglitazone layer and the sodium starch glycolate comprises about 10 to about 20% of the total weight of the pioglitazone layer.

3. The pharmaceutical dosage form as described in claim 1 wherein the dosage form exhibits a $C_{max}$ for the pioglitazone that is at least 135% of the $C_{max}$ for the immediate release pioglitazone tablet.

4. The pharmaceutical dosage form as described in claim 1 wherein the dosage form exhibits an AUC for the pioglitazone that is at least 120% of the AUC for the immediate release pioglitazone tablet.

* * * * *